(12) United States Patent
Dean

(10) Patent No.: US 6,349,412 B1
(45) Date of Patent: Feb. 26, 2002

(54) MEDICAL COOLING VEST AND SYSTEM EMPLOYING THE SAME

(75) Inventor: W. Clark Dean, Simsbury, CT (US)

(73) Assignee: Hamilton Sundstrand Corporation, Windsor Locks, CT (US)

( * ) Notice: Subject to any disclaimer, the term of this patent is extended or adjusted under 35 U.S.C. 154(b) by 0 days.

(21) Appl. No.: 09/707,133

(22) Filed: Nov. 6, 2000

(51) Int. Cl.$^7$ .................................................. A41D 1/04
(52) U.S. Cl. ........................................................ 2/102
(58) Field of Search ........................... 2/102, 272, 458, 2/81, 97

(56) References Cited

U.S. PATENT DOCUMENTS 3,610,323 A * 10/1971 Troyer .......................... 165/46
4,738,119 A * 4/1988 Zafred ........................ 62/259.3
4,998,415 A * 3/1991 Larsen ........................ 62/231
5,438,707 A * 8/1995 Horn ............................... 2/69
6,178,562 B1 * 1/2001 Elkins ............................ 2/458

FOREIGN PATENT DOCUMENTS

GB          2032255 A  *  5/1980  ........... A62B/17/00

* cited by examiner

*Primary Examiner*—John J. Calvert
*Assistant Examiner*—Robert H. Muromoto, Jr.

(57) ABSTRACT

Leakage problems in a cooling system for use by medical personnel during surgery are avoided in a vest that includes a sealed, coolant receiving space through which coolant may pass. A source of liquid coolant at ambient pressure is connected to the space and a suction producing device is connected to an outlet for the space for drawing coolant from the source through the space at sub-atmospheric pressure. As a consequence, coolant will not leak from the vest in the event a leak develops. The vest may be formed of two flexible membranes sealed to each other to define the space and is provided with a coolant permeable spacer within the coolant space within the vest to prevent the membranes from collapsing upon each other.

34 Claims, 5 Drawing Sheets

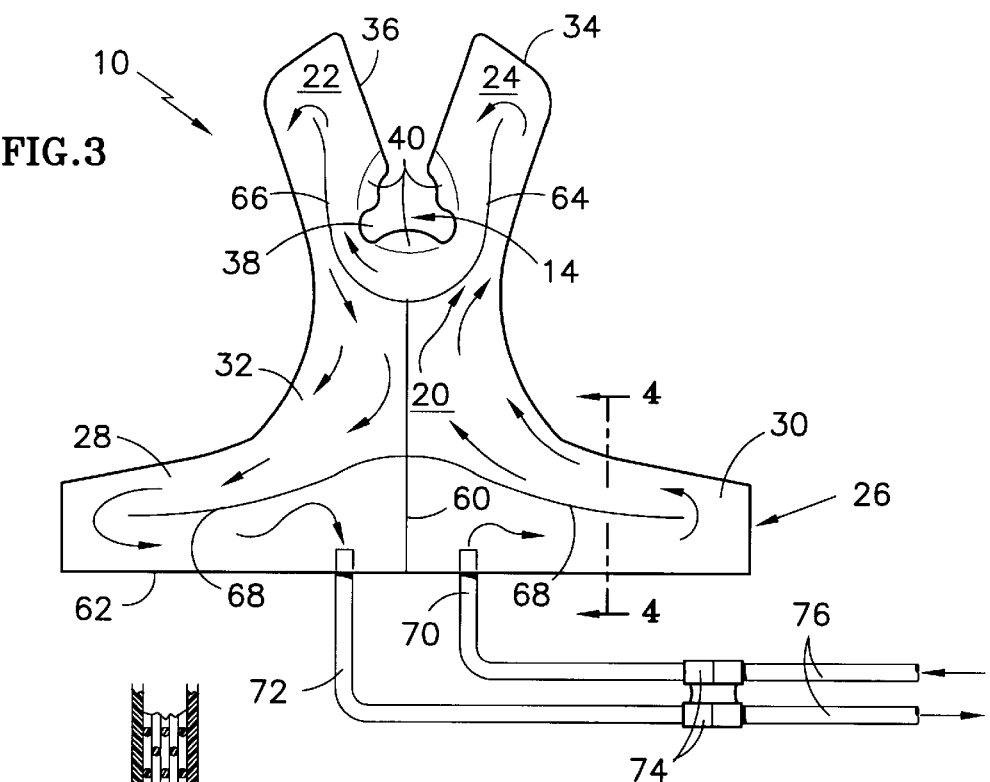
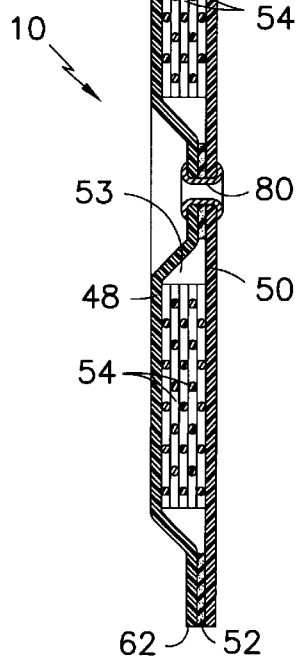
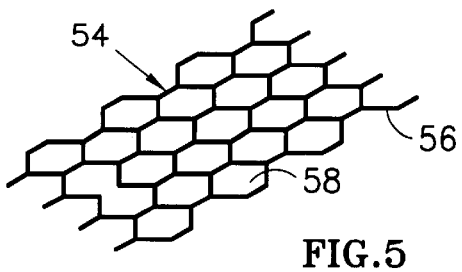

MEDICAL COOLING VEST AND SYSTEM EMPLOYING THE SAME

FIELD OF THE INVENTION

This invention relates to a vest for use by medical personnel during the course of surgery and to a system with which the vest may be used.

BACKGROUND OF THE INVENTION

Medical operating room environments are maintained at a relatively cool temperature to keep the operating room staff comfortable. However, a comfortable temperature for the surgeon and support staff is not always the best temperature for the patient who can suffer hypothermia in a cold operating room environment. One remedy for this problem is to warm the patent with a disposable, heated blanket. In some cases, excessive heat is still lost from the patient at the actual site of the operation. On the other hand, if the operating room were kept at a warmer temperature, patient temperature could be maintained at a proper level, but the surgeons would be uncomfortably hot as would be operating room staff.

One proposed solution to the problem is to provide a cooling garment for the surgeon and/or operating room staff. One such garment consists of cooling water tubes sewn into a compliant vest of open mesh fabric worn next to the skin of the wearing. Cooling water from the existing operating room chiller flows through the tubes to carry away heat and keep the surgeon comfortable while the open mesh fabric of which the vest is made allows perspiration to escape. However, the complexity of the construction of such a garment makes the manufacturing cost excessive. Moreover, the cost factor is exacerbated as several sizes of the garment are required to fit the full range of body sizes of the wearers of the garment. In addition, the spacing between the tubes provides uneven heat transfer from the user's skin.

Another such garment alternatively used to cool race car drivers consists of two layers of thermoplastic membrane material heat sealed together to form a serpentine flow path for cooling water. The pressure of the water inflates the passages to allow flow. This geometry reduces the cost of the vest, but the nature of the membrane material, particularly when inflated with cooling water, does not allow full compliance of the vest to the body curvature of the wearer. Moreover, the non-permeable nature of the membrane severely impedes the evaporation of perspiration from the skin of the wearer.

Furthermore, these garments can pose an additional hazard for the patient. The coolant is pumped through the garment to a coolant reservoir forming part of the operating room chiller. The latter is at atmospheric pressure and in order to cause flow of the coolant, the pump elevates the pressure of the coolant to induce flow. As a result, the coolant within the garment and associated conduits is at a pressure somewhat above atmospheric pressure. In the event the system springs a leak, it is possible that the coolant, which might not be sterile, could spray on the surgeon causing a distraction. Even more significantly, the coolant may spray on the patient in the area of the site of the operation giving rise to the possibility of infection or the like.

The present invention is directed to overcoming one or more of the problems.

SUMMARY OF THE INVENTION

It is a principal object of the invention to provide a new and improved cooling vest for use by medical personnel during surgical procedures. It is also a principal object of the invention to provide a system, including a cooling vest, that eliminates the possibility of leakage of coolant from the vest and the consequences that flow therefrom.

According to one facet of the invention, there is provided a cooling vest for medical personnel that includes a vest body having a top opening for the head of a wearer and opposed side openings for the arms of the wearer. The vest body includes at least two flexible membranes sealed to each other to define a coolant receiving space. At least one coolant inlet is provided to the space along with at least one coolant outlet. A coolant permeable, flexible spacer is disposed between the membranes within the space for preventing the membranes from collapsing upon one another.

In one embodiment of the invention, the spacer is a thin layer of flexible open celled foam.

In another embodiment, the spacer includes at least one flexible, generally helical coil. Still another embodiment of the invention contemplates that the spacer include at least one flexible grid. By way of example, plastic hexagonal mesh is one such material.

In a highly preferred embodiment, the vest consists of a single vest panel including the membranes, the coolant outlet, the coolant inlet and the flexible spacer. Alternatively, an alternate embodiment contemplates that the vest comprise at least two panels with each of the panels including the membranes, the coolant outlet, the coolant inlet and the flexible spacer. In the preferred embodiment, adjustable straps employing velcro, buckles, or the like, interconnects parts of the single vest panel in an adjustable fashion to allow the same to be sized to fit wearers of varying statures. In this embodiment, adjustment straps are located at the chest area of the panel, its sides and at the front. In the alternate embodiment, the adjustable straps interconnect the various panels to form the vest body so that one vest body may be sized to fit wearers of varying statures.

In both embodiments, the invention contemplates that some of the straps be connected to the respective panel parts or the individual panels inwardly of the adjacent sides or tops thereof so that the sides or tops of adjacent panel parts or adjacent panels may overlap to accommodate a wearer of small stature.

The preferred embodiment of the invention contemplates that the membranes be formed of a semi-permeable material as for example, the stretched, polytetrafluoroethylene film containing minute pores, an example of which is sold under the registered trademark "GORE-TEX". This material allows moisture in gaseous form to pass through the film to thereby be drawn away from the skin of the wearer. It is also a two way stretch material, allowing the vest to readily conform to the body of the wearer, even when the vest panel or panels contain coolant.

A preferred embodiment includes an interior, membrane separating structure. Preferably, the same is a multi-layer, hexagonal plastic net separation structure. The same may also include an interior, adhesive membrane sealant line or lines to channel coolant flow in a desired flow path.

In the alternate form of the invention, as mentioned previously, plural vest panels are employed in the preferred form of the alternate embodiment and includes first, second and third panels. The first panel is a U-shaped top panel and the second and third panels are right side and left side panels respectively. The right and left side panels are connected, at their tops, to the right and left-hand sides of both the forward edge and a rearward edge of the first panel while the left and right sides of the right panel are connected respectively to the right and left side of the left side panel.

In the alternate embodiment, there are plural ones of the inlet spaced from one another and a coolant distributor interconnects the inlets. Similarly, in the alternate embodiment, there are plural ones of the outlet spaced from one another and the vest further includes a coolant collection manifold interconnecting the outlets.

In an alternate embodiment, the collection manifold and/or the distributor include a flexible tube located within the space between the membranes.

According to another facet of the invention, a cooling system for medical personnel for use during surgery is provided. The system includes a vest adapted to be worn by medical personnel to cover the torso and includes a top opening for disposition about the neck of the wearer and two oppositely directed, side openings for receipt of the arms of the wearer. A sealed, coolant receiving space is disposed within the vest and defines a flow path within the vest through which coolant may pass. The space has at least one inlet and at least one outlet. Also provided is a source of liquid coolant at ambient pressure connected to the inlet and a suction producing device connected to the outlet. The suction producing device draws coolant from the source through the space within the vest at sub-atmospheric pressure and returns the coolant to the source. As a consequence of this construction, should a leak come into existence, coolant will not leak to the exterior of the vest. Rather, ambient air, which does not affect operation, will be drawn into the coolant flow path.

In one embodiment, the flow path includes at least one tube. In another embodiment, the vest includes at least two flexible membranes sealed to each other to define the space and the flow path.

In a preferred embodiment the membranes are semi-permeable, allowing perspiration to be drawn away from the wearer into the coolant flow path.

In a highly preferred embodiment of the invention, the suction producing device includes an ejector. Preferably, the ejector includes a first inlet connected to the coolant source and an outlet also connected to the coolant source. A pump is provided for pumping coolant from the source to the first inlet. A second inlet is located between the first inlet and the ejector outlet and is connected to the outlet of the vest. As a consequence, the ejector creates a negative pressure at the second inlet to draw coolant at sub-ambient pressure through the vest.

Another embodiment contemplates a suction producing device in the form of a pump wherein the outlet of the pump is connected to the source of coolant and the inlet or suction side of the pump is connected to the vest outlet.

Other objects and advantages will become apparent from the following specification taken in connection with the accompanying drawings.

DESCRIPTION OF THE DRAWINGS

FIG. 3 is a plan view illustrating the configuration of a vest panel employed in the preferred embodiment of a vest made according to the invention and additionally illustrating, in schematic form, the plumbing of the vessel;

FIG. 4 is an enlarged, fragmentary sectional view typical of any given part of the panel illustrated in FIG. 3;

FIG. 5 is a perspective view of a hexagonal, plastic mesh utilized in the vest;

DESCRIBED OF THE PREFERRED EMBODIMENTS

Figure 1:
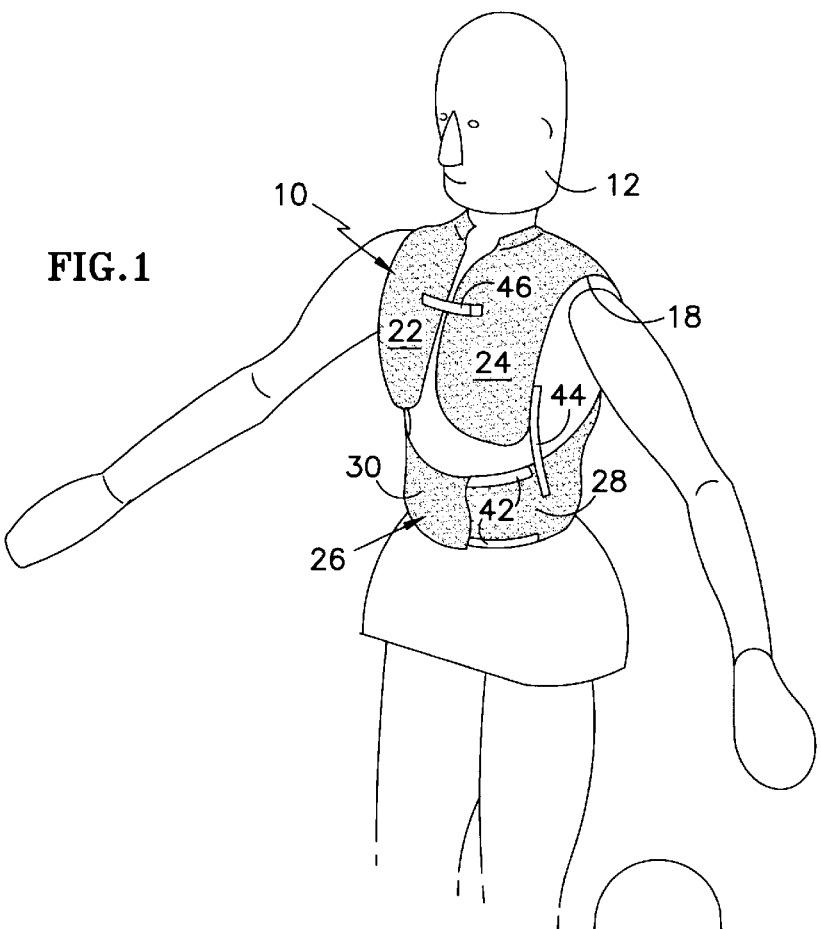
FIG. 1 is a somewhat schematic, perspective view of an exemplary and preferred embodiment of a vest made according to the invention fitted to a wearer and taken from above and to the right side of the wearer.

A highly preferred embodiment of a medical cooling vest made according to the invention is illustrated in FIGS. 1–5 of the drawings. With initial reference to FIGS. 1–3 inclusive, the same is seen to include a single panel, generally designated 10, configured to fit about the torso or the mid-section of a wearer 12. The panel 10 includes a neck opening 14, a right arm opening 16 and a left arm opening 18. The panel 10 further includes a back part 20, right and left front parts 22, 24, respectively and a mid-section encircling part, generally designated 26. Referring specifically to FIG. 3, the panel 10 is shown in greater detail. The same is in the form of an inverted T having lower, opposed, oppositely extending arms 28, 30 which define a mid-section encircling part 26, and an upstanding base 32 integral with the arms 26 and 28. The base 32 has an end 34 remote from the arms 28, 30 and in which is centrally located a generally keyhole shaped slot 36. The slot 36 thus divides the base end 34 into the right front part 24 and the left front part 22 while defining the neck receiving opening 14 as well. As best seen in perhaps in FIGS. 2 and 3, the innermost part of the keyhole slot 36 is designated 38 and is provided with inwardly extending flaps 40 which are collar like to embrace the neck of the wearer 12.

Figure 2:
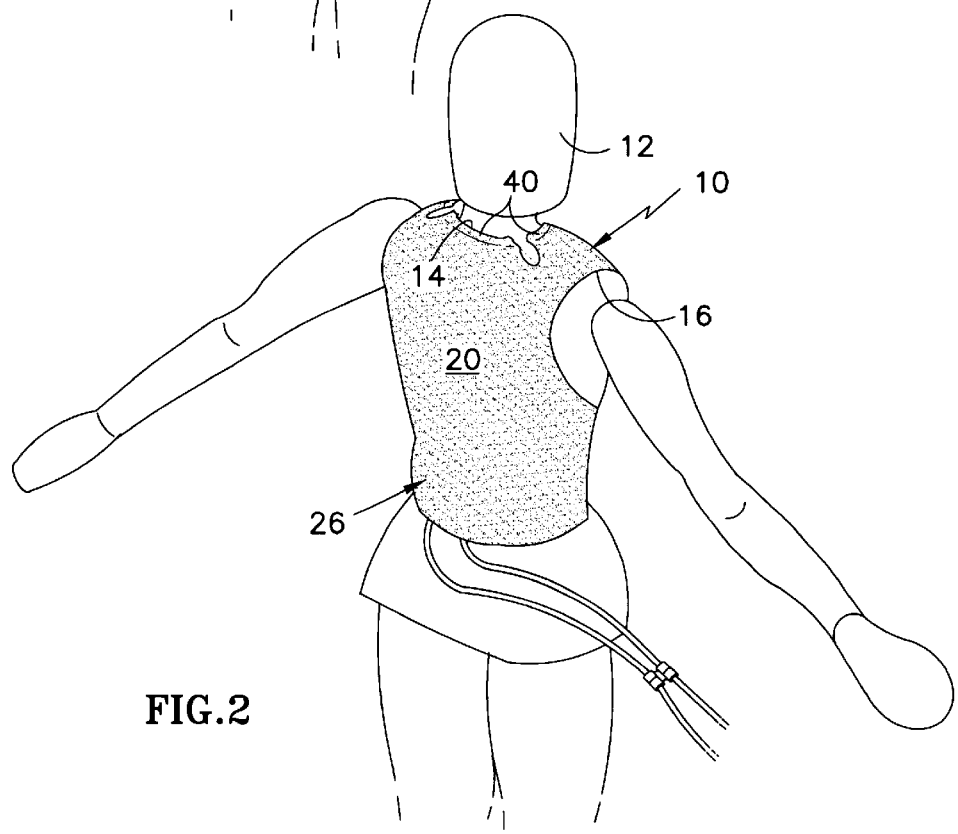
FIG. 2 is a view of the preferred embodiment similar to FIG. 1 but taken from the rear, upper right side of the wearer.
Figure 12:
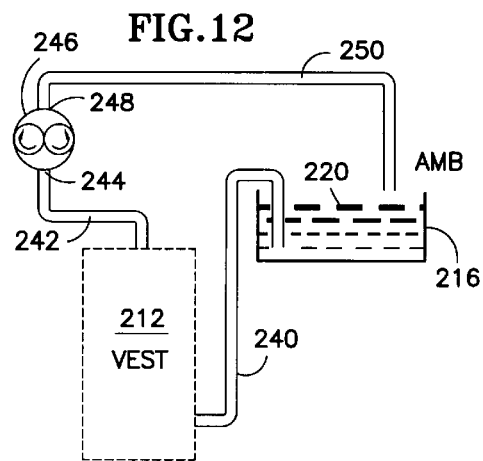
FIG. 12 is a schematic of another embodiment of suction producing device that may be connected to either embodiment of the vest.

As can be ascertained from the consideration of FIGS. 1 and 2 on the one hand and FIG. 3 on the other hand, the single panel 10 is thus shaped so that when the neck of the wearer is received in the innermost part of the keyhole slot 36, the left and right parts 24 of the base end 34 will fit over the shoulders of the wearer as shown in FIG. 12 to cover the upper part of the torso. The back part 20 completely covers the back of the wearer while the arms 28, 30 may be wrapped around the mid-section of the wearer at approximately waist level or somewhat higher. Conventional, adjustable straps may be employed to maintain the vest in the desired configuration on the wearer. For example, straps 42 may be employed to secure either one of the arms 28, 30 and overlapping relation to the other while straps 44 (only one of which is shown) may be employed to secure the right and left parts 22, 24 to the arms 28, 30. Similarly, a strap 46 may be located just below the neck receiving opening to secure the sides of the keyhole slot 36 to one another.

The straps 42, 44, 46 may be conventional, i.e., formed of a flexible fabric or the like and employing buckles to provide an adjustable connection. Alternatively, the straps may be provided with velcro-like material to achieve the same purpose. The straps may be bonded to the panel 10 or, more preferably, held in place by grommets as will be described in greater detail hereinafter. It is of significance that the point of attachment of the straps to the panel 10 be inwardly of the edges thereof so that the various parts 20, 22, 24, 26 of the panel 10 may overlap when necessary to accommodate a wearer 12 of small stature. At the same time, when the wearer is of large stature, gaps between the various parts of the panel such as are visible in FIG. 1, may exist.

Turning now to FIGS. 4 and 5, the panel 10 will be described in greater detail. The same is made of up two film like membranes 48, 50 which may be bonded at their edges as indicated at 52 by a weld or an adhesive or the like. The membranes 48 and 50 are preferably, though not necessarily, made of a material that will stretch in two directions and which even more preferably is semi-permeable to moisture. One such material is constructed of a knitted synthetic fiber cloth with a stretchable membrane heat sealed to one side such as that manufactured and sold under the trademark "GORE-TEX". The stretchability of such a material allows the vest formed by the panel 10 to conform to the various curves of the body of the wearer. At the same time, because it is semi-permeable, perspiration developing between the vest and the wearer may be drawn away from the wearer for increased comfort.

For reasons to be seen, coolant is flowed between the membranes 48 and 50 at sub-atmospheric pressure. Thus, in order to prevent the membranes 48, 50 from collapsing on one another, the space 52 between the same, which serves as a flow space for a liquid coolant, is filled with a permeable spacer 54. In a highly preferred embodiment, the spacer 54 is formed of several layers of a mesh that is flexible. For example, a flexible plastic mesh 54 formed of strands 56 defining a plurality of hexagonal openings 58 may be used in multiple layers. Other forms of spacers as, for example, a flexible open cell foam can be employed as well but it is preferred to use a mesh.

Returning to FIG. 3, by means of welds or baffles extending between the membranes 48, 50, the flow of coolant may be directed. For example, one such baffle is shown at 60 and extends centrally from the lower edge 62 of the panel 10 upwardly towards the keyhole slot 36 stopping short thereof and terminating in two additional baffles 64,68 which extend approximately midway upwardly through the right side part 24 and left side part 22, stopping short of the end 34. In addition, a baffle 68 may be located in each of the arms 28, 30, extending from the central baffle 60 almost to the ends of each of the arms 28 and 30. On one side of the central baffle 60, at the lower edge 62 of the panel 10, an inlet tube 70 is connected. A similar, outlet tube 72 is located on the other side of the central baffle 60. Both extend to quick disconnect fittings 74 which connect to additional hoses 76 which may be connected to a coolant circulation system as will be seen hereinafter. Thus, a cooling liquid is introduced through the inlet 70 and flows in the direction of arrows completely about all parts of the vest to exit the same via the outlet 72 to be returned to the circulating system.

It is noted that this means of connection provides an umbilical-like cord that is connected to the rear of the panel 10 so that it will be out of the way of the wearer when the vest is in use. The baffles 60, 64, 66, 68 may be formed by welds such as the weld 52 or by bonding as desired. Alternatively, an adhesive matrix 78 as shown in FIG. 4 may be employed.

At desired locations, a grommet 80 is employed to connect the membranes 48, 50 together. This prevents the same from separating substantially and allowing coolant to pool in lower most parts of the vest or when, by accident, pressure of the coolant between the membranes 48 and 50 exceeds atmospheric pressure. The grommets 80 may also be employed to secure the ends of the straps 42, 44, 46 to the panel 10 at the desired locations.

The embodiment of the vest just described is a preferred embodiment of the invention in that a single panel may be employed to define the vest. Two different sizes of the panels 10 will be sufficient to accommodate the overwhelming majority of potential wearers because the various parts 22,24,26,28 may overlap with one another to accommodate wearers of small stature or may separate somewhat as mentioned previously to accommodate wearers of large stature. The use of a semi-permeable membrane such as "GORE-TEX" and the fact that the space 52 between the membranes 48, 50 is at sub-atmospheric pressure in normal operation and allows perspiration to be drawn through the membranes into the circulation system provides an added measure of comfort for the wearer. The provision of the neck flaps 40 provide still another greater measure of comfort for the wearer and the stretchy nature of the membranes allows good conformance of the vest to the curves of the body of the wearer. The use of the mesh shown in FIG. 5 in several layers provides good separation between the membranes 48 and 50 during operation while allowing free flow of coolant through the vest. Yet, by reason of the flexible nature of the strands 56 defining the mesh, the vest remains flexible so as not to interfere with the movements of the wearer. It further allows good conformance of the vest to the curves of the wearer.

Figure 6:
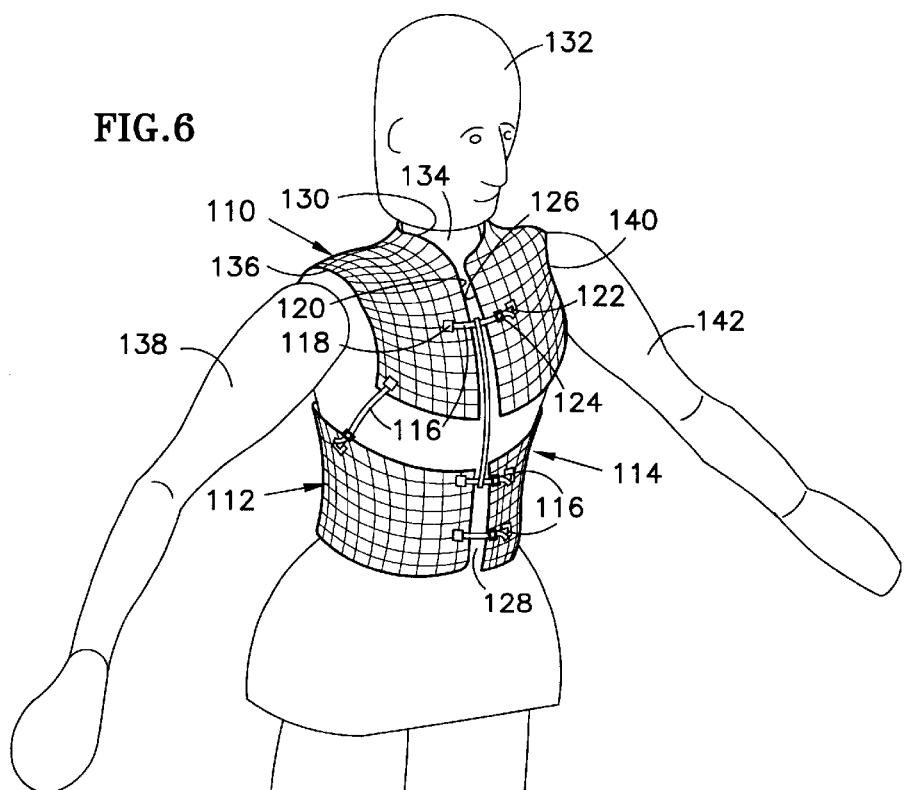
FIG. 6 is a somewhat schematic, perspective view of a vest made according to an alternate embodiment of the invention fitted to a wearer and taken from above and to the right side of the wearer.
Figure 7:
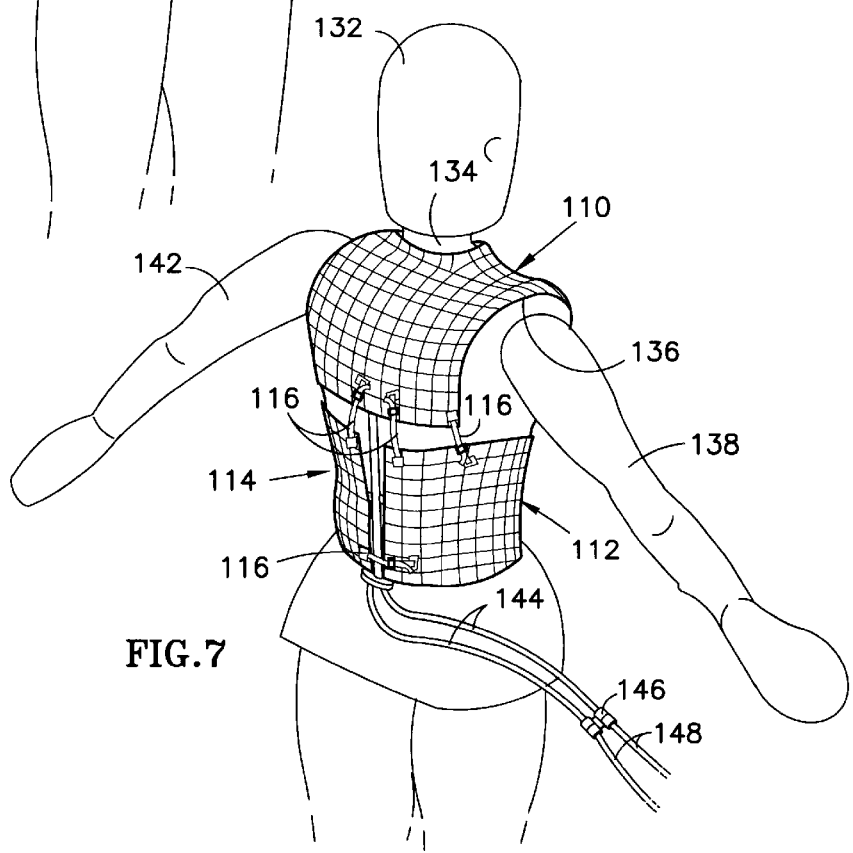
FIG. 7 is a view of the alternate embodiment similar to FIG. 6 but taken from the rear, upper right side of the wearer.

An alternate embodiment of a medical cooling vest made according to the invention is illustrated in FIGS. 6–10 of the drawings and with initial reference to FIGS. 6 and 7, is seen to be made up of three panels including a top panel, generally designated 110, a right side panel, generally designated 112, and a left side panel, generally designated 114. The panels are secured to one another by adjustable straps, shown schematically at 116 which may be generally conventional in construction. That is to say, they will typically include an elongated flexible strap, typically of fabric, on one panel and a mating buckle on a facing panel for adjustably receiving the strap. As illustrated in FIG. 6, a point of securement 118 for the straps 116 is shown spaced inwardly of an edge 120 of the top panel 110. A point of attachment 122 for a buckle shown schematically at 124 is likewise supported inwardly of another edge 126 of the top panel. The purpose of this configuration is to allow the edges of the panels to overlap to accommodate a wearer of small stature. For wearers of larger stature, the edges of the various panels facing one another may be separated by spaces, as, for example, shown at 128 in FIG. 1.

The vest has an upper opening 130 through which the head 132 of the wearer may extend. The opening 130 surrounds the neck 134 of the wearer.

The vest also includes a right side opening 136 through which the right arm 138 of the wearer may extend and a similar opening 140 through which the left arm 142 may extend.

Near the bottom of the back of the vest, an umbilical cord 144 is located. The same may include a quick disconnect fitting 146 to a similar cord 148 which is connected to a system for circulating coolant through the vest as will be described in greater detail hereinafter.

Figure 8:
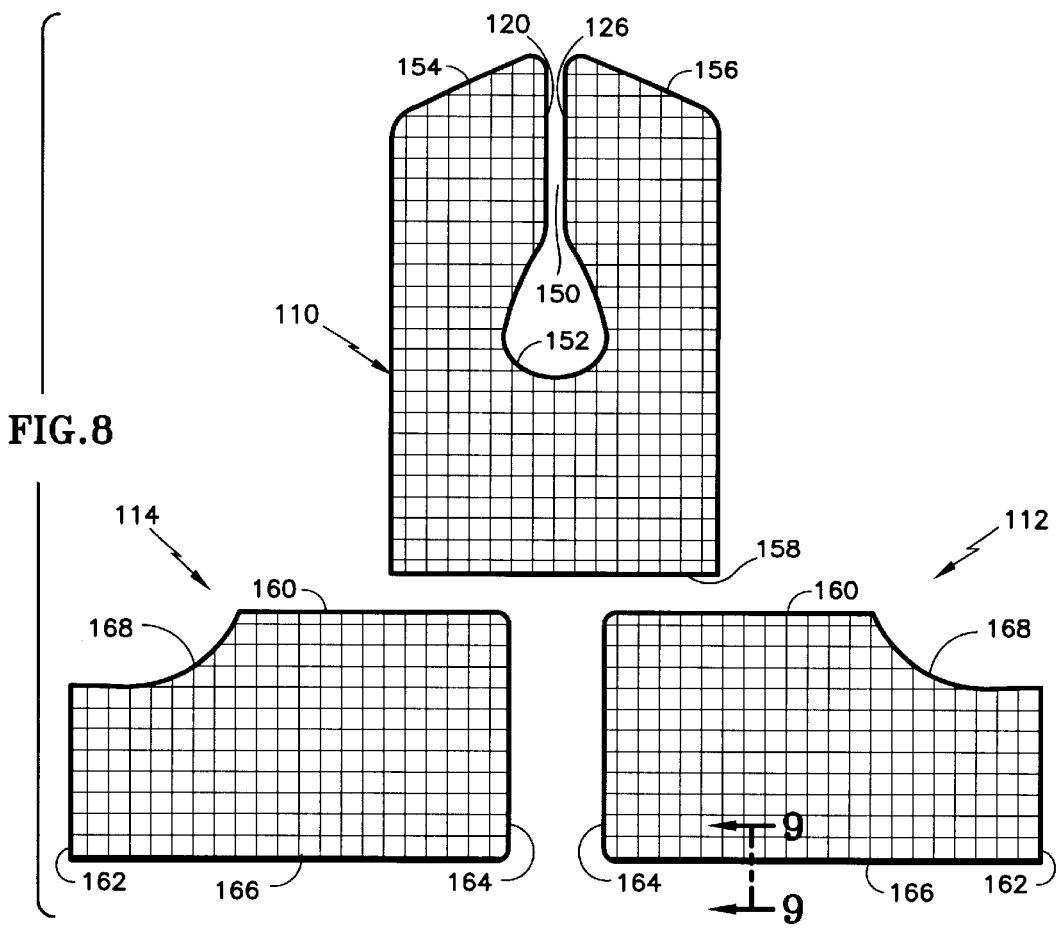
FIG. 8 is a view illustrating the configuration of vest panels employed in making up the alternate embodiment of a vest made according to the invention.

Turning now to FIG. 8, the basic configuration of the panels 110,112,114 will be described. The top panel 110 is generally U-shaped and includes an elongated slit 150 terminating in a round opening 152 in the center of the panel. The round opening 152 defines the neck receiving opening 130 while the slit 150 is defined by the edges 120 and 126 mentioned previously. The panel 110 has front side edges 154 and 156 on either side of the slit 150 and a rear side edge 158. The edge 154 is on the left side of the top panel 110 while the edge 156 is one the right side of the front panel 110.

The side panels 112 and 114 are mirror images of one another so only the panel 112 will be described in detail. It has a top side edge 160, a front side edge 162, a rear side edge 164 and a bottom edge 166. An arcuate cut-out 168 interconnects the top side edge 160 and the right side edge 162 to partially form the openings 136, 140. As noted above, the left side panel 114 is a mirror image of the panel 112 and its edge 164 corresponds to a rear side edge while its edge 162 corresponds to a front side edge.

The strap and buckle connections along with the umbilical cord 144 have been omitted from FIG. 8 for clarity.

Figure 9:
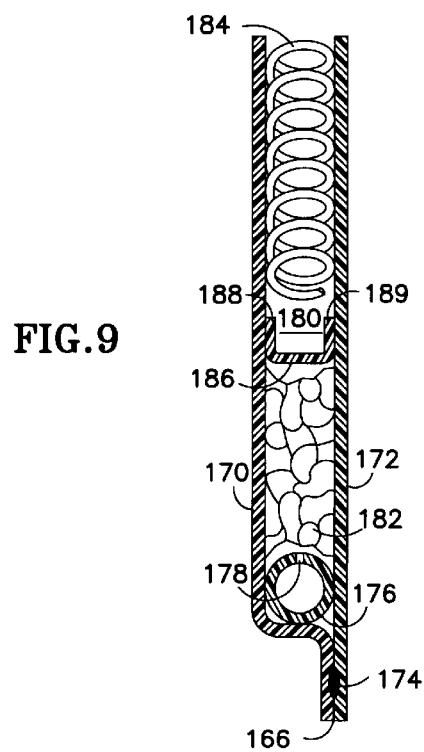
FIG. 9 is an enlarged, fragmentary sectional view of one of the panels taken approximately along the line 9—9 in FIG. 8.

FIG. 9 is an enlarged, fragmentary view taken along the line 9—9 in FIG. 8. It is representative of the construction of each of the panels 110, 112 and 114. The same shows each panel 110, 112, 114, to be made up of two membranes 170 and 172 which are bonded together by any suitable bond such as an adhesive, a weld, or the like shown schematically at 174. The bond produces a seal at about the entire periphery of each of the panels immediately adjacent the edges 160, 162, 164, 166.

The membranes 170, 172 are formed of a flexible material which preferably may stretch or flex in two mutually perpendicular directions. Again, they may be formed of a rubber or other elastomeric film or a two directional stretch fabric such as the fabric sold under the trademark "SPANDEX" that has been impregnated with a material such as a silicone elastomer to provide a seal. As a preferred alternative, the membranes 170, 172 may be formed of a material such as that sold under the registered trademark "GORE-TEX".

Just inside the edges of each of the panels, at locations to be described hereinafter, as well as centrally through certain of the panels, a flexible elastomeric tube 176 is located. The tubes 176 may serve as a coolant distributor to the space between the membranes 170, 172 or as a collection manifold for coolant in that space. To that end, ports 178 are located in the tubing 176 at desired locations to serve as inlets or outlets to the space 180 between the membranes 170, 172. It is desirable that the space 180 be made as small as possible, particularly in terms of the dimension between the membranes 170, 172 which basically defines the thickness of the vest. The greater this dimension, the greater the volume of the space 180 and the greater the volume of coolant the same may hold. Of course, an increased coolant volume means an increased weight of the vest. Since such weight will act upon the wearer of the vest, it is desired to minimize it as much as possible so that the weight does not fatigue the wearer or otherwise interfere with free movement of the wearer.

As will be seen, in a highly preferred system employing the vest, it is desirable that the space 180 be at a pressure that is less than atmospheric pressure. Thus, in order to maintain separation between the membranes 170, 172 to accommodate coolant in the space 180, spacers are located between the membranes 170, 172. One type of spacer is shown at 182 in the form of an open celled flexible foam having an average cell size of, perhaps, $1/16$ of an inch. Ambient pressure acting on the membranes 170, 172 drive it against the spacer 182 which maintains separation while, because of its open celled nature, flow of the coolant through the space 180 is allowed.

An alternative type of spacer is also shown in FIG. 9 in the form of a flexible, helical coil 184. In practice, a grid made up of several strands of the helical coil 184 will be employed. In other instances, a sheet of lightweight flexible material formed and cut in the pattern of conventional expanded metal with suitable surface grooves interconnecting the various cells may be used as an alternative.

In order to prevent an increase in the distance between the membranes 170, 172, expansion limiters such as shown at 186 may be employed. The expansion limiters may be generally channel-shaped having one leg 188 bonded to the membrane 170 and another leg 190 bonded to the membrane 172. The expansion limiters 188 prevent the vest from blowing up like a balloon in the event the pressure of the incoming coolant, for some reason, becomes positive with respect to the ambient atmosphere. They may also be advantageously employed, if elongated, to act as flow directors or baffles to channel flow within the various panels to achieve a uniformity of flow, and thus a uniformity of cooling for the wearer. Furthermore, they prevent expansion that could be caused as by pooling of the coolant near the lower edges of each of the panels simply under the action of gravity.

Figure 10:
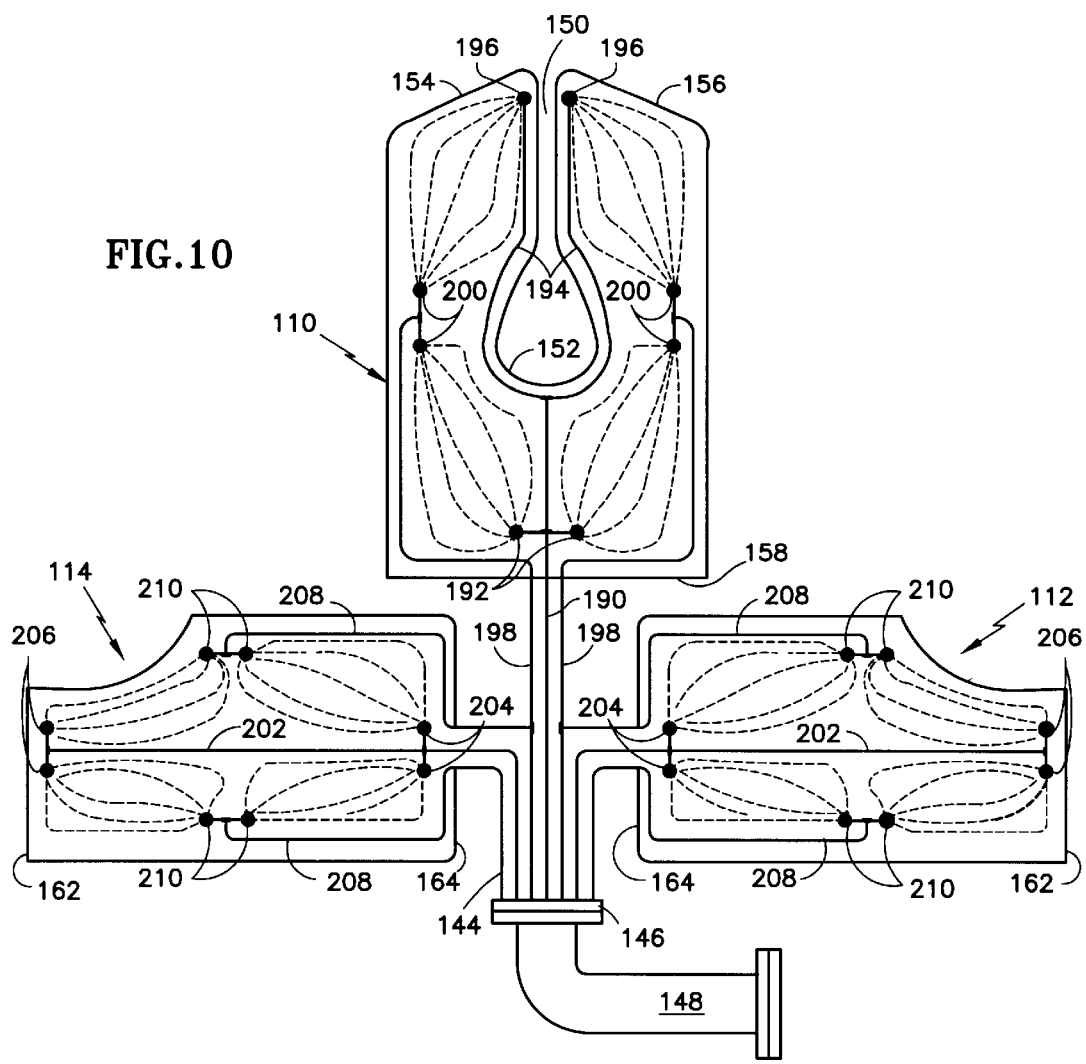
FIG. 10 is a plumbing schematic of the alternate embodiment.

FIG. 10 schematically illustrates a preferred plumbing arrangement for the vest. A flexible tube 190 that enters the panel 110 serves as an inlet conduit for the coolant to that panel. Adjacent the edge 158 and generally centrally of the panel, two of the inlets 192 are located. The tube 190 extends toward the circular opening 152 where it splits into two lines 194. The two lines 194 flank the slit 150 to extend to the front edges 154, 156 where two additional inlets to the space 180 are located.

A pair of return tubes 198 flank the tube 190 and extend along the edges of the panel 110 to approximately the mid point. Each of the lines 198 terminates in two outlets to return coolant through the umbilical 144 in a fashion to be seen.

Each of the side panels 112, 114, have a central inlet tube 202 of flexible material which provides two inlets 204 adjacent the edge 164 and two additional inlets 206 adjacent the edge 162.

Two outlet conduits 208, also of flexible tubing, enter the panel through the edge 164 and extend to about the mid point of the panel to terminate in respective outlets 210 as well. As a result, flow patterns such as those indicated by the dotted lines in FIG. 10 exist with the coolant flowing from the inlets to the respective outlets at a sub-atmospheric pressure as will be seen. It is to be particularly noted that, as alluded to previously, the flow patterns can be mandated through the use of the extension limiters 186 as baffles if desired. At the same time, baffles partly or wholly separate from the extension limiters may be used.

Figure 11:
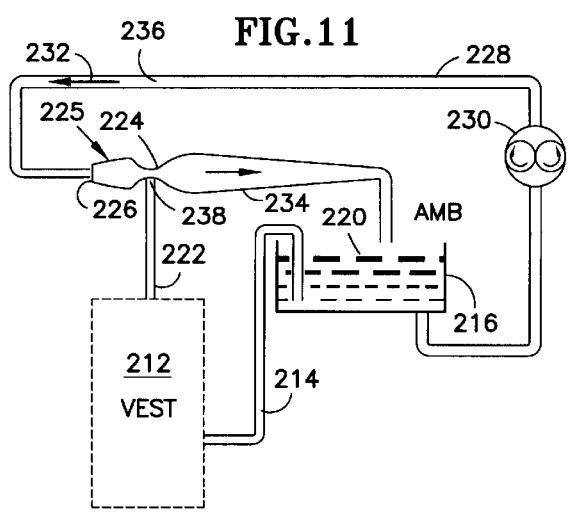
FIG. 11 is a schematic illustrating one form of a suction producing device that may be connected to an outlet of either embodiment of the vest.

FIG. 11 illustrates a system employing a vest 212 which may be made according to the invention or made according to the prior art if desired. The system illustrated in FIG. 11 is designed to cause fluid within the vest 212 to be at a sub-atmospheric pressure so that if a leak occurs, air will be sucked into the coolant flow path rather than coolant expelled from the vest. Thus, an inlet tube forming part of the umbilical 148 and designated 214 connects the vest 212 to a reservoir 216 containing the coolant to be employed. This will conventionally be part of the typical operating room chiller unit found in most hospital operating rooms. It is to be particularly noted that the coolant 220 in the reservoir 216 is at ambient pressure.

An outlet conduit 222 extends from the vest 212 to the neck 224 of an ejector 225 venturi. That is to say, the ejector 225 has an inlet at its neck 224. A second inlet 226 is connected via a conduit 228 to a pump 230 which in turn is connected to the reservoir 216. The pump is arranged to pump coolant from the reservoir in the direction of an arrow 232 into the inlet 226 of the ejector 225.

The ejector 225 also includes an outlet 234 which is connected via a return line 236 to the reservoir 216.

In operation, the pump forces coolant through the ejector 225 which operates conventionally to draw fluid from an inlet 238 at the neck 224 and inject it into the flowing stream. That is to say, the ejector 225 acts as a suction producing device, thereby lowering the pressure at the line 222 to a sub-atmospheric level. Because of the pressure drop associated with fluid flow within conduits, and the fact that ambient pressure exists at the reservoir 216, through the vest 212, the coolant will be at a sub-atmospheric pressure to prevent the same from exiting the vest 112 in the event of a leak. To the extent air is drawn into the vest, it will not inhibit proper operation of the system. Specifically, the air will pass with the coolant from the vest and will be vented from the system when the air reaches the reservoir 216.

An alternate system is illustrated in FIG. 12. Where like components are employed, like reference numerals are utilized. In this case, a conduit 240 extends from the reservoir 216 to the inlet of the vest while an outlet conduit 242 extends to the inlet or suction side 244 of a pump 246. The outlet side 248 of the pump 246 is connected by a conduit 250 to return to the reservoir 216. Again, the pump 246 acts as a suction producing device and causes the coolant within the vest 212 to always be at sub-atmospheric pressure.

From the foregoing, it will be appreciated that a vest made according to the invention as well as the system of the invention are highly advantageous. The vest may be made of relatively simple construction in comparison to those type vests heretofore suggested employing a plurality of tubes for circulation of a coolant within the vest. The use of spacers between membranes allows the cooling flow to be uniformly exposed to the entire surface area of the vest providing uniform heat transfer from the wearer and avoiding the non-uniform heat transfer of tube type vests. The use of a stretch material with a semi-permeable membrane allows the vest to conform to the curved surfaces of the wearer's body while condensing perspiration into the circulating cooling fluid to improve comfort and lower the humidity and uncontrolled condensation under surgical gowns. It also avoids the non-uniform contact and non-breathing characteristics of heat sealed thermoplastic vests. The same is readily sizeable to medical personnel of varying statures through the unique arrangement of the straps and buckles and the use of overlapping single or multiple vest panels. The vest is ideally suited for use in systems where the coolant is under sub-atmospheric pressure when it flows through the vest by reason of the presence of the spacers. At the same time, the vest may be used with positive pressure systems by reason of the use of the extension limiters. Moreover, the extension limiters can be employed to serve a dual function, namely the limiting of the extension of the space between the two membranes as well as baffles or flow directors. This further simplifies construction.

The system of the invention is applicable to vests of varying constructions, including those utilizing internal tubing for controlling coolant circulation. The fact that the coolant passes through the vest at a sub-atmospheric pressure during use of the system avoids the problem of leakage of coolant onto the surgeon or the patient during operation. Moreover, the same advantageously employs the already existing operating room chiller, requiring basically only a connection to its reservoir and the addition of a suction producing device such as the ejector or the location of the already existing system pump so that its suction side is connected to the outlet of the vest.

I claim:

1. A cooling system for medical personnel for use during surgery, comprising:
    a vest adapted to be worn by medical personnel to cover the torso and including a top opening for disposition about the neck of the wearer and two oppositely directed, side openings for receipt of the arms of the wearer;
    a sealed coolant receiving space within the vest defining a flow path within the vest through which coolant may pass;
    at least one inlet to said space;
    at least one outlet from said space;
    a source of liquid coolant at ambient pressure connected to said inlet; and
    a suction producing device connected to said outlet for drawing coolant from said source through said space at sub-atmospheric pressure and returning the coolant to said source.

2. The cooling system of claim 1 wherein said flow path includes at least one tube.

3. The cooling system of claim 1 wherein said vest includes at least two flexible membranes sealed to each other to define said space and said flow path.

4. The cooling system of claim 3 further including a coolant permeable spacer within said space to prevent said membranes from collapsing upon each other.

5. The cooling system of claim 4 wherein said spacer is a thin layer of open cell foam.

6. The cooling system of claim 4 wherein said spacer includes at least one, flexible generally helical coil.

7. The cooling system of claim 4 wherein said spacer includes at least one, flexible grid.

8. The cooling system of claim 1 wherein said vest comprises at least two separate panels adjustably connected together by straps.

9. The cooling system of claim 1 wherein said vest consists of a single panel having parts thereof adjustably connected to each other by straps.

10. The cooling system of claim 1 wherein said suction producing device includes an ejector.

11. The cooling system of claim 10 wherein said ejector includes a first inlet connected to said coolant source, an outlet connected to said source, a pump for pumping cooling from said source to said first inlet and a second inlet located between said first inlet and said ejector outlet and connected to said outlet from said space.

12. The cooling system of claim 1 wherein said suction producing device includes a pump.

13. A cooling vest for medical personnel to be worn during surgical procedures comprising:
    a vest body having a top opening for the head of a wearer and opposed side openings for the arms of the wearer;
    said vest body including at least two flexible membranes sealed to each other to define a coolant receiving space;

at least one coolant inlet to said space;

at least one coolant outlet from said space; and a coolant permeable, flexible spacer between said membranes within said space for preventing said membranes from collapsing upon one another.

14. The cooling vest of claim 13 wherein said spacer is a thin layer of flexible open cell foam.

15. The cooling vest of claim 13 wherein said spacer includes at least one, flexible generally helical coil.

16. The cooling vest of claim 13 wherein said spacer includes at least one, flexible grid.

17. The cooling vest of claim 13 wherein said spacer is a multilayer flexible mesh.

18. The cooling vest of claim 17 wherein said mesh has hexagonal shaped openings.

19. The cooling vest of claim 13 wherein said vest consists of a single panel including said membranes, said coolant outlet, said coolant inlet and said flexible spacer.

20. The cooling vest of claim 19 wherein said single panel has a periphery shaped generally as an inverted T having oppositely directed arms adapted to encircle the mid-section of a wearer and an upright base extending therefrom, said base, at an end remote from said arms, having a keyhole slot with a slot end located inwardly of said base end adapted to at least partially encircle the neck of a wearer.

21. The cooling vest of claim 20 wherein said slot end includes collar like flaps for embracing the neck of a wearer.

22. The cooling vest of claim 20 further including straps for adjustably connecting said arms together in encircling relation about the mid-section of a wearer and located so that parts of at lest one of said arms may overlap the other of said arms.

23. The cooling vest of claim 22 further including straps for adjustably connecting opposite sides of said base end to said arms.

24. The cooling vest of claim 20 further including straps for adjustably connecting opposite sides of said base end to said arms.

25. The cooling vest of claim 13 wherein said vest comprises at least two vest panels, each of said panel including said membranes, said coolant outlet, said coolant inlet and said flexible spacer; and adjustable straps interconnecting said panels to form said vest body.

26. The cooling vest of claim 25 wherein there are first, second and third panels, said first panel being a U-shaped panel and said second and third panels being right side and left side panels respectively, said right and left side panels being connected, at their tops to the right and left sides of both a forward edge, and a rearward edge of the first panel, the left and right sides of said right side panel being connected respectively to the right and left side of said left side panel.

27. The cooling vest of claim 26 wherein at least some of said straps are connected to respective panels inwardly of the adjacent sides or tops thereof so that said sides or tops of adjacent panels may overlap to accommodate a wearer of small stature.

28. The cooling vest of claim 13 wherein there are plural ones of said inlets spaced from one another, and further including a coolant distributor interconnecting said inlets.

29. The cooling vest of claim 13 wherein there are plural ones of said outlets spaced from one another and further including a coolant collection manifold interconnecting said outlets.

30. The cooling vest of claim 29 wherein there are plural ones of said inlets spaced from one another, and further including a coolant distributor interconnecting said inlets.

31. The cooling vest of claim 28 wherein said distributor includes a flexible tube within said space.

32. The cooling vest of claim 29 wherein said collection manifold includes a flexible tube within said space.

33. The cooling vest of claim 13 further including separation limiters within said space and interconnecting both said membranes to limit enlargement of the space by separation of the membranes.

34. A cooling vest for medical personnel to be worn during surgical procedures comprising:

a vest body having a top opening for the head of a wearer and opposed side openings for the arms of the wearer;

said vest body including at least two flexible semipermeable membranes sealed to each other to define a coolant receiving space;

at least one coolant inlet to said space;

at least one coolant outlet from said space; and a coolant permeable, flexible spacer between said membranes within said space for preventing said membranes from collapsing upon one another.

* * * * *